US012642597B2

(12) United States Patent
Herrmann et al.

(10) Patent No.: US 12,642,597 B2
(45) Date of Patent: Jun. 2, 2026

(54) TECHNIQUE FOR DETERMINING A NEED FOR A RE-REGISTRATION OF A PATIENT TRACKER

(71) Applicant: Stryker European Operations Limited, Carrigtwohill (IE)

(72) Inventors: Florian Herrmann, Schwanau (DE); Emeric Umbdenstock, Freiburg (DE); Fadi Ghanam, Schallstadt (DE)

(73) Assignee: Stryker European Operations Limited, Carrigtwohill (IE)

( * ) Notice: Subject to any disclaimer, the term of this patent is extended or adjusted under 35 U.S.C. 154(b) by 644 days.

(21) Appl. No.: 18/097,393

(22) Filed: Jan. 16, 2023

(65) Prior Publication Data

US 2023/0225797 A1     Jul. 20, 2023

(30) Foreign Application Priority Data

Jan. 18, 2022     (EP) ..................................... 22151995

(51) Int. Cl.
   *A61B 34/20*          (2016.01)
   *G16H 30/20*         (2018.01)
   *G16H 40/67*         (2018.01)
(52) U.S. Cl.
   CPC ............. *A61B 34/20* (2016.02); *G16H 30/20* (2018.01); *G16H 40/67* (2018.01); *A61B 2034/2048* (2016.02); *A61B 2034/2055* (2016.02)
(58) Field of Classification Search
   CPC ....................................................... A61B 5/06
   See application file for complete search history.

(56) References Cited

U.S. PATENT DOCUMENTS

| 9,226,799 B2 | 1/2016 | Lightcap et al. |
| 9,235,765 B2 | 1/2016 | Bentley et al. |

(Continued)

FOREIGN PATENT DOCUMENTS

| DE | 102011054730 A1 | 4/2013 |
| EP | 3181085 A1 | 6/2017 |

(Continued)

OTHER PUBLICATIONS

English language abstract and machine-assisted English translation for DE 10 2011 054 730 A1 extracted from espacenet.com database on Jan. 18, 2023, 11 pages.

(Continued)

*Primary Examiner* — Angela M Hoffa
(74) *Attorney, Agent, or Firm* — Howard & Howard Attorneys PLLC

(57)          ABSTRACT

A technique for determining a need for a re-registration of a patient tracker with medical image data of a patient is presented. The patient tracker comprises an acceleration sensor configured to generate inertial data indicative of an acceleration of the patient tracker. A method implementation of the technique comprises the following steps performed by a processor: receiving inertial data acquired by the acceleration sensor, analyzing the received inertial data, or data derived therefrom, with respect to at least one first predetermined condition indicative of a drift of the tracker or an impact on the tracker, and generating, when the at least one first predetermined condition is fulfilled, at least a first re-registration signal.

17 Claims, 16 Drawing Sheets

(56)                    References Cited

U.S. PATENT DOCUMENTS

| | | | | |
|---|---|---|---|---|
| 10,799,299 B2* | 10/2020 | Lee | | A61B 90/39 |
| 10,828,112 B2* | 11/2020 | Syverson | | A61B 34/76 |
| 10,905,496 B2* | 2/2021 | Zuhars | | A61B 34/20 |
| 11,291,507 B2* | 4/2022 | Stawiaski | | A61B 34/70 |
| 11,660,148 B2* | 5/2023 | Walen | | A61B 34/76 |
| | | | | 606/87 |
| 11,717,353 B2* | 8/2023 | Zuhars | | A61B 34/20 |
| | | | | 606/86 R |
| 11,806,090 B2* | 11/2023 | Stawiaski | | A61B 34/20 |
| 11,877,808 B2* | 1/2024 | Syverson | | A61B 90/00 |
| 12,279,834 B2* | 4/2025 | Colbrunn | | A61B 34/32 |
| 12,343,092 B2* | 7/2025 | Walen | | A61B 34/10 |
| 12,394,086 B2* | 8/2025 | Joshi | | G06F 3/041 |
| 2006/0070439 A1 | 4/2006 | Kwon et al. | | |
| 2007/0034731 A1 | 2/2007 | Falco | | |
| 2008/0200844 A1* | 8/2008 | Millahn | | A61B 90/90 |
| | | | | 600/595 |
| 2012/0154604 A1 | 6/2012 | Chen et al. | | |
| 2014/0111608 A1 | 4/2014 | Pfeil | | |
| 2017/0224425 A1 | 8/2017 | Lee et al. | | |
| 2018/0193097 A1 | 7/2018 | Mclachlin et al. | | |
| 2018/0199999 A1* | 7/2018 | Syverson | | A61B 34/30 |
| 2019/0011709 A1 | 1/2019 | Yadav et al. | | |
| 2019/0090955 A1 | 3/2019 | Singh et al. | | |
| 2019/0357986 A1 | 11/2019 | Morgan et al. | | |
| 2020/0011669 A1 | 1/2020 | Seth | | |
| 2020/0015909 A1* | 1/2020 | Stawiaski | | G06T 7/74 |
| 2020/0197105 A1 | 6/2020 | Wu | | |
| 2020/0237441 A1* | 7/2020 | Zuhars | | A61B 34/20 |
| 2021/0030479 A1 | 2/2021 | Marti et al. | | |
| 2021/0045815 A1* | 2/2021 | Syverson | | A61B 90/00 |
| 2021/0128252 A1* | 5/2021 | Zuhars | | A61B 34/20 |
| 2021/0212769 A1* | 7/2021 | Walen | | A61B 34/10 |
| 2021/0360100 A1 | 11/2021 | Nazzaro et al. | | |
| 2022/0175467 A1* | 6/2022 | Stawiaski | | A61B 34/20 |
| 2023/0225796 A1* | 7/2023 | Herrmann | | A61B 34/20 |
| | | | | 600/424 |
| 2023/0248443 A1* | 8/2023 | Colbrunn | | A61B 90/03 |
| | | | | 700/255 |
| 2023/0293246 A1* | 9/2023 | Walen | | A61B 34/76 |
| | | | | 606/87 |
| 2023/0329833 A1* | 10/2023 | Sharifi-Mehr | | A61B 17/00 |
| 2023/0368330 A1* | 11/2023 | Joshi | | G06T 7/55 |
| 2023/0368418 A1* | 11/2023 | Joshi | | A61B 34/20 |
| 2024/0008933 A1* | 1/2024 | Stawiaski | | A61B 34/20 |
| 2024/0090954 A1* | 3/2024 | Syverson | | A61B 34/76 |
| 2024/0115325 A1* | 4/2024 | Calloway | | G06N 3/045 |
| 2025/0195159 A1* | 6/2025 | Prakhya | | A61B 34/30 |

FOREIGN PATENT DOCUMENTS

| | | |
|---|---|---|
| KR | 20130137435 A | 12/2013 |
| WO | 2017185170 A1 | 11/2017 |
| WO | 2018049196 A1 | 3/2018 |
| WO | 2020012479 A1 | 1/2020 |

OTHER PUBLICATIONS

English language abstract and machine-assisted English translation for KR 20130137435 A extracted from espacenet.com database on Jan. 18, 2023, 10 pages.

\* cited by examiner

Receive inertial data acquired by a first acceleration sensor of a first tracker Analyze the received inertial data, or data derived therefrom, with respect to at least one first predetermined condition Generate, when the at least one first predetermined condition is fulfilled, at least a first re-registration signal

400

410

420

430

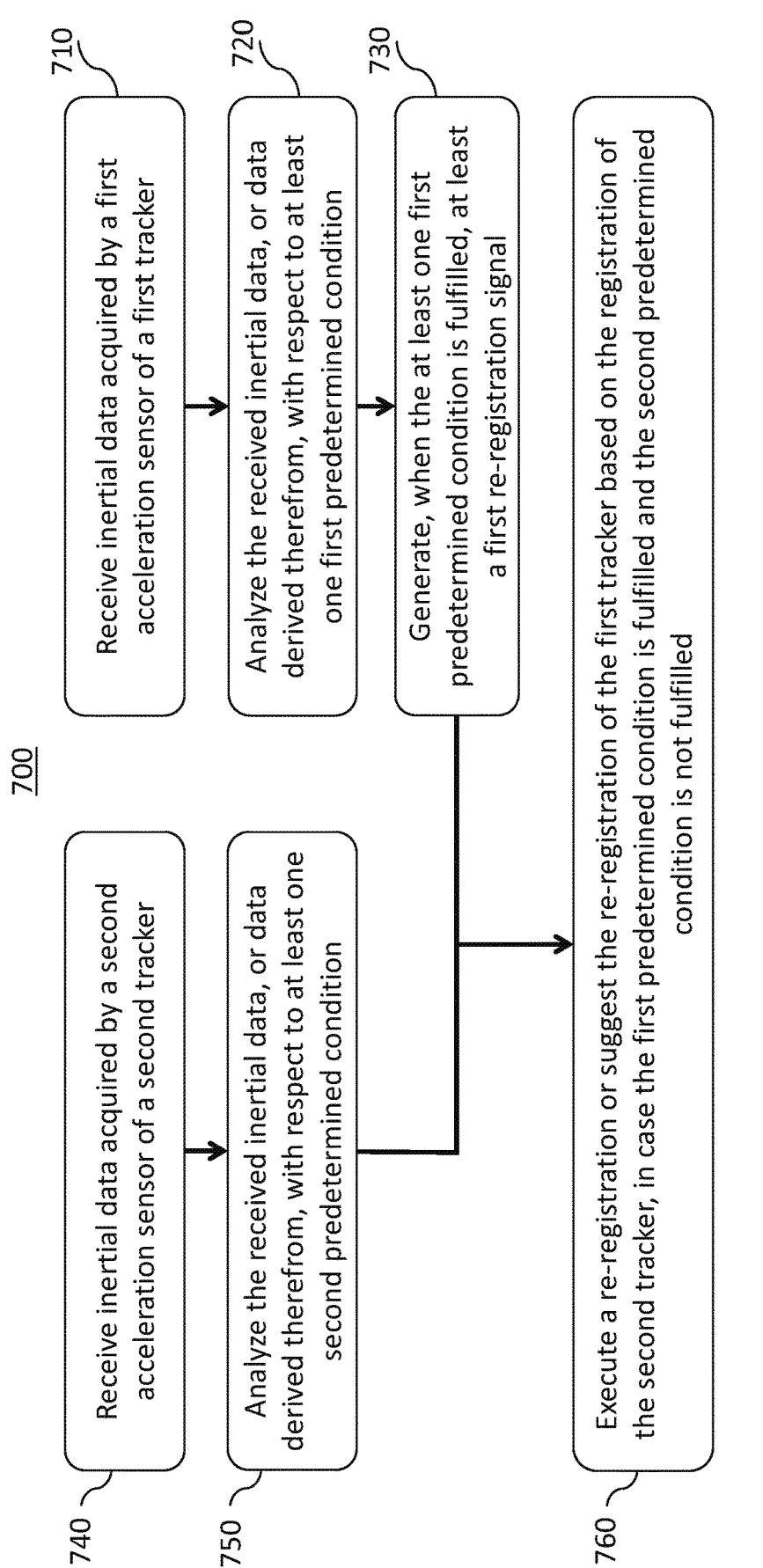

710 Receive inertial data acquired by a first acceleration sensor of a first tracker 720 Analyze the received inertial data, or data derived therefrom, with respect to at least one first predetermined condition 730 Generate, when the at least one first predetermined condition is fulfilled, at least a first re-registration signal 740 Receive inertial data acquired by a second acceleration sensor of a second tracker 750 Analyze the received inertial data, or data derived therefrom, with respect to at least one second predetermined condition 760 Execute a re-registration or suggest the re-registration of the first tracker based on the registration of the second tracker, in case the first predetermined condition is fulfilled and the second predetermined condition is not fulfilled

TECHNIQUE FOR DETERMINING A NEED FOR A RE-REGISTRATION OF A PATIENT TRACKER

PRIORITY CLAIM

This application claims priority under 35 U.S.C. § 119 to European Patent Application No. 22151995.2, filed Jan. 18, 2022, the entire contents of which are hereby incorporated by reference.

TECHNICAL FIELD

The present disclosure generally relates to the field of surgical tracking. In particular, a processor-implemented method for determining a need for a re-registration of a tracker attached to a patient is presented. Also presented are a computer program product, a data processing system configured to perform the method, and a system comprising the data processing system.

BACKGROUND

Various surgical tracking techniques are used for assisting a surgeon or controlling operation of a surgical robot. For example, medical image data of a patient may be visualized on a display and overlaid with a model, position or trajectory of a handheld surgical tool tracked by a tracking system. As another example, a robot arm holding a surgical tool may be navigated relative to a tracked bony structure such as a vertebra.

In such scenarios, trackers are typically attached to the patient anatomy and to the surgical tool. Image data registration is performed in a first step for determining a pose of the patient tracker relative to patient image data obtained by a medical imaging modality, e.g., a computer tomography scanner. In a second step, the relative position between the patient tracker and the tracked surgical tool is determined. As a result, the relative position between the patient image data and the surgical tool can be determined and visualized for a surgeon or used for robot control.

For achieving a proper surgical result, it is mandatory that tracking is performed at a high degree of accuracy, since any tracking error may result in harming the patient. To acquire such high degree of accuracy, it is required to not only initially determine a patient tracker position but to also monitor tracker movements. In US 2019/0090955 A1, an updated pose of a tracker comprising an inertial measurement unit (IMU) is determined by combining first data from a registration process with second data acquired by the IMU and third data acquired by an imaging device, e.g., a camera.

While a tracker pose may be updated in near real-time, any tracker movement relative to the patient anatomy the patient tracker is attached to will render a previous registration between the patient tracker and the patient image data incorrect. Using an incorrect registration will result in incorrect information regarding the relative position between the patient anatomy and the patient tracker. In case of an incorrect registration, an updated tracker pose will provide incorrect information regarding the relative position between the patient anatomy and the patient tracker, which puts the patient at health risks during surgery.

Different approaches for reducing the risk of using such an incorrect registration have been proposed. For example, an initial registration may be updated by executing a registration procedure repeatedly at regular time intervals. However, repeating a registration at regular time intervals may result in unnecessarily executing registrations when the previous registration is still valid. As such, the duration of a surgical intervention will unnecessarily be extended. In other cases, a surgeon may be operating based on an incorrect registration until the next registration is performed. Thus, there is a tradeoff between reducing the probability of a surgeon operating based on an incorrect registration, i.e., by increasing the frequency of the repeated registrations, and increasing the duration of a surgery due to unnecessarily performing repeated registrations.

Further, not every movement of a patient tracker renders a previous registration incorrect. For example, the patient or a table the patient is placed on can be moved intentionally and in a controlled way. If the relative position between the patient tracker and the patient anatomy the tracker is attached to remains fixed during such movements, a previous registration will still be valid, and a re-registration is unnecessary. In case the patient tracker is intentionally moved, a trained surgeon may also be able to manually decide if a re-registration is necessary or not. However, there also exist cases of unintended tracker movements relative to the patient anatomy, e.g., due to surgical personnel or instrumentation bumping against a patient tracker. Especially when such unintended impacts take place unnoticed by the surgeon, there is an increased risk of the surgeon working based on an incorrect patient tracker registration, which, as stated above, leads to significant health risks for the patient.

SUMMARY

There is a need for a technique for efficiently determining a need for a re-registration of a tracker attached to a patient.

According to a first aspect, a method for determining a need for a re-registration of a first tracker attached to a patient with medical image data of the patient is provided. The first tracker comprises a first acceleration sensor configured to generate inertial data indicative of an acceleration of the first tracker. The method comprises the following steps performed by a processor: receiving inertial data acquired by the first acceleration sensor of the first tracker, analyzing the received inertial data, or data derived therefrom, with respect to at least one first predetermined condition indicative of at least one of a drift of the first tracker and an impact on the first tracker, and generating, when the at least one first predetermined condition is fulfilled, at least a first re-registration signal.

The need for a re-registration may be related to a movement between the first tracker and a patient anatomy the first tracker is attached to. The movement may result in a sudden or gradual movement between the first tracker and the patient anatomy. Moreover, there may also be "virtual" movements (e.g., due to processing or sensor artefacts) that indicate a need for a re-registration, which in practice does not exist.

The first tracker may be attached to a vertebra or other bony or non-bony anatomic structure. The first tracker may be attached only to a surface of the anatomic structure, for example using a clamp or an adhesive.

The first and any further acceleration sensor may be configured to individually or in combination generate inertial data for one or more degrees of freedom (DOFs). As an example, the acceleration sensor, or a combination of acceleration sensors, may be configured to generate inertial data for 2, 3, 4, or 6 DOFs. The first and any further acceleration sensor may be configured as, or comprised by, an IMU. The first and any further acceleration sensor, in particular the IMU, may comprise at least one of an accelerometer and a gyroscope.

The at least one first predetermined condition may enable identifying one or different sources of acceleration of the first tracker based on the generated inertial data. The main sources of tracker acceleration may comprise positional drift of the tracker, e.g., due to a tracker clamp not being strong enough to fixedly attach the tracker to the patient anatomy, and an impact on the tracker, e.g., due to a surgeon or a robot bumping against the tracker. A positional drift may be associated with an acceleration that is typically lower than an acceleration due to an impact on the tracker.

According to one variant, the at least one first predetermined condition may comprise at least one threshold decision. In one example, the at least one first predetermined condition may comprise a combination of multiple (e.g., successive or parallel) threshold decisions. The at least one threshold decision may be based on a first decision threshold of at least 5 m/s$^2$ (e.g., at least 7 m/s$^2$ or at least 10 m/s$^2$). Such a first decision threshold may be indicative of an impact on the first tracker if the generated inertial data indicate that the first decision threshold is exceeded.

Additionally or alternatively, the inertial data received from the first acceleration sensor, or data derived therefrom, is indicative of an angular acceleration. The at least one threshold decision may be based on a second decision threshold based on the data indicative of the angular acceleration. The at least one threshold decision may be based on a combination of the first decision threshold and the second decision threshold. The at least one threshold decision may be based on a combination of at least one of the first decision threshold and the second decision threshold with at least a third decision threshold, e.g., for a duration of the tracker movement or a duration during which the acceleration is detected.

Further additionally, or alternatively, the at least one first predetermined condition may be associated with an acceleration indicative of a movement pattern. Analyzing the received inertial data, or data derived therefrom, with respect to at least one first predetermined condition may comprise deriving a movement pattern from the received inertial data and comparing the derived movement pattern to at least one first predetermined movement pattern. The predetermined movement pattern may be a predefined movement over time, e.g., a damped oscillation having a certain behavior as defined by the at least one first predetermined condition.

According to one variant, at least the first re-registration signal may trigger a first re-registration notification. The first re-registration notification may be at least one of an acoustic notification and an optical notification. The first re-registration notification may be a user notification suggesting a re-registration. The first re-registration notification may be output until a user input is received as a reaction to the notification.

According to one variant, a notification device may be configured to receive at least the first re-registration signal and output the first re-registration notification. The notification device may be part of the first tracker. The notification device may be a status light emitting diode (LED) or a tracking LED. The status LED or tracking LED may be switched to a different mode, e.g., a different color or a different operation frequency, when the notification device receives at least the first re-registration signal. Alternatively or additionally, the notification device may be part of a computer system comprising, e.g., a display configured to visualize information for a surgeon, or a loudspeaker, or an augmented reality device (such as a head-mounted display, HMD).

According to one variant, the method may further comprise monitoring the notification device for the first re-registration notification, and generating at least a second re-registration signal upon detecting the first re-registration notification. At least the second re-registration signal may trigger one of a re-registration and a user notification suggesting the re-registration. The second re-registration signal may be output by a computer system, e.g., a display configured to visualize information for a surgeon, or a loudspeaker, or an augmented reality device (such as an HMD).

A first tracker coordinate system associated with the first tracker (e.g., with the actual tracker or image data thereof) may have previously been registered with a medical image coordinate system associated with the medical image data. In such a scenario, at least the second re-registration signal may trigger one of re-registering the first coordinate system with the medical image coordinate system and suggesting the re-registration, e.g., to a surgeon. The medical image data may comprise medical image data acquired via one of magnetic resonance imaging (MRI), ultrasound imaging, X-ray projection imaging, angiography and computed tomography (CT). The suggestion of the re-registration may comprise at least one of an optical and acoustic signal. In one example, the re-registration may be suggested via a pop-up window shown on a display in the field of view of a surgeon.

Additionally or alternatively, the second re-registration signal may be transmitted to a computer system for reporting the first re-registration notification. The second signal may be transmitted via a wired or wireless connection.

According to another variant, a first tracker coordinate system associated with the first tracker (e.g., with the actual tracker or image data thereof) may have been registered with a medical image coordinate system associated with the medical image data. At least the first re-registration signal may trigger one of re-registering the first coordinate system with the medical image coordinate system and suggesting the re-registration, e.g., to a surgeon.

According to one variant, a second tracker comprising a second acceleration sensor may be attached to the patient. A second tracker coordinate system associated with the second tracker (e.g., with the actual tracker or image data thereof) may have been registered with the medical image coordinate system. The method may further comprise receiving inertial data acquired by the second acceleration sensor of the second tracker, and analyzing the received inertial data, or data derived therefrom, with respect to at least one second predetermined condition indicative of at least one of a drift of the second tracker and an impact on the second tracker. In case of the first predetermined condition being fulfilled and the second predetermined condition not being fulfilled, a re-registration may be executed or suggested based on the registration of the second tracker coordinate system with the medical image coordinate system. Executing a re-registration based on an existing registration may be less time consuming and may need less computational power than a new registration not based on an existing registration.

The drift of the first tracker may comprise at least one of a positional drift of the first tracker and an integration drift of the first acceleration sensor. The positional drift is directed at a (e.g., gradual) change of the position of the first tracker relative to a patient anatomy the tracker is attached to. The positional drift may be detected to span a certain period of time (e.g., by applying a corresponding temporal threshold decision). In addition, detection of the positional drift may require at least one of exceeding a minimum acceleration threshold and not exceeding a maximum acceleration threshold.

The integration drift may be based on a virtual position error that accumulates over time to reach a critical value if it is not reset or compensated. Since positional information is obtained by integrating acceleration information twice over time, the main error source is error afflicted acceleration information. Said error afflicted acceleration information may result from, e.g., sensor noise, sensor signal offset and/or sensor orientation error of the first acceleration sensor. Since the integration drift accumulates over time, inertial data, or data derived therefrom, indicative of the integration drift has a typical, e.g., a linear, form that can easily be detected.

According to one implementation, at least the first tracker may be imaged in camera image data continuously taken by a camera system. The method may further comprise visualizing the camera image data at least for a point in time corresponding to a detected impact. The image data may be continuously recorded in a ring buffer or similar memory structure. Visualizing the recording, or a portion thereof, may be triggered or suggested upon generation of the first or the second re-registration signal. For this purpose, the respective one of the first and second re-registration signal used for triggering visualization of the recording may comprise a time stamp, and similar temporal information may be associated with the camera image data. The visualization of the image data associated with a detected impact may facilitate decision-making of a surgeon, e.g., regarding the need of a suggested re-registration as described above.

According to one variant, the method may comprise analyzing the camera image data for a positional change of the first tracker. In this case, the first re-registration signal may be generated in case a positional change of the first tracker is identified based on the camera image data while the first predetermined condition is fulfilled.

The camera system may comprise a third acceleration sensor configured to generate inertial data indicative of an acceleration of the camera system. The method may comprise receiving, from the third acceleration sensor, inertial data, and analyzing the received inertial data, or data derived therefrom, with respect to at least one third predetermined condition indicative of an impact on the camera system. The first re-registration signal may then be generated in case the inertial data generated by the third acceleration sensor is not indicative of an impact on the camera system while the first predetermined condition is fulfilled.

The camera image data and the inertial data indicative of an acceleration of the camera system may both be received and analyzed, either in parallel or in sequence.

In this case, the first re-registration signal may be generated in case a movement of the first tracker is identified based on the image data and, at the same time, the inertial data generated by the third acceleration sensor is not indicative of an impact on the camera system while the first predetermined condition is fulfilled.

In this way, a relative movement between the first tracker and the camera system may be detected via optically tracking the first tracker. The detected relative movement may then be verified via the inertial data received from the acceleration sensor of the camera system. The camera system may comprise a stereo camera configured to optically survey a surgical environment (such as an operating room or a part thereof). As a result, the accuracy of the determination of the need for a re-registration may be increased.

According to a second aspect, a computer program product is provided. The computer program product comprises instructions configured to perform the steps of the method described herein, when the computer program product is executed on one or more processors.

According to a third aspect, a data processing system for determining a need for a re-registration of a first tracker attached to a patient with medical image data of the patient is provided. The first tracker comprises a first acceleration sensor configured to generate inertial data indicative of an acceleration of the first tracker. The data processing system comprising a processor configured for receiving inertial data acquired by the first acceleration sensor of the first tracker, analyzing the received inertial data, or data derived therefrom, with respect to at least one first predetermined condition indicative of at least one of a drift of the first tracker and an impact on the first tracker, and generating, when the at least one first predetermined condition is fulfilled, at least a first re-registration signal.

The processor of the data processing system may be configured to perform the steps of any variant of the method as described herein.

According to another aspect, a surgical system is provided. The surgical system comprises the data processing system according to the third aspect and a camera system configured to image at least the first tracker that is imaged in camera image data continuously taken by the camera system.

BRIEF DESCRIPTION OF THE DRAWINGS

Further features and advantages of the method, the computer program product and the data processing system presented herein are described below with reference to the accompanying drawings, in which:

FIG. 3B illustrates a flow diagram of another variant of the method for detecting a need of re-registration for a patient tracker;

DETAILED DESCRIPTION

Figure 1A:
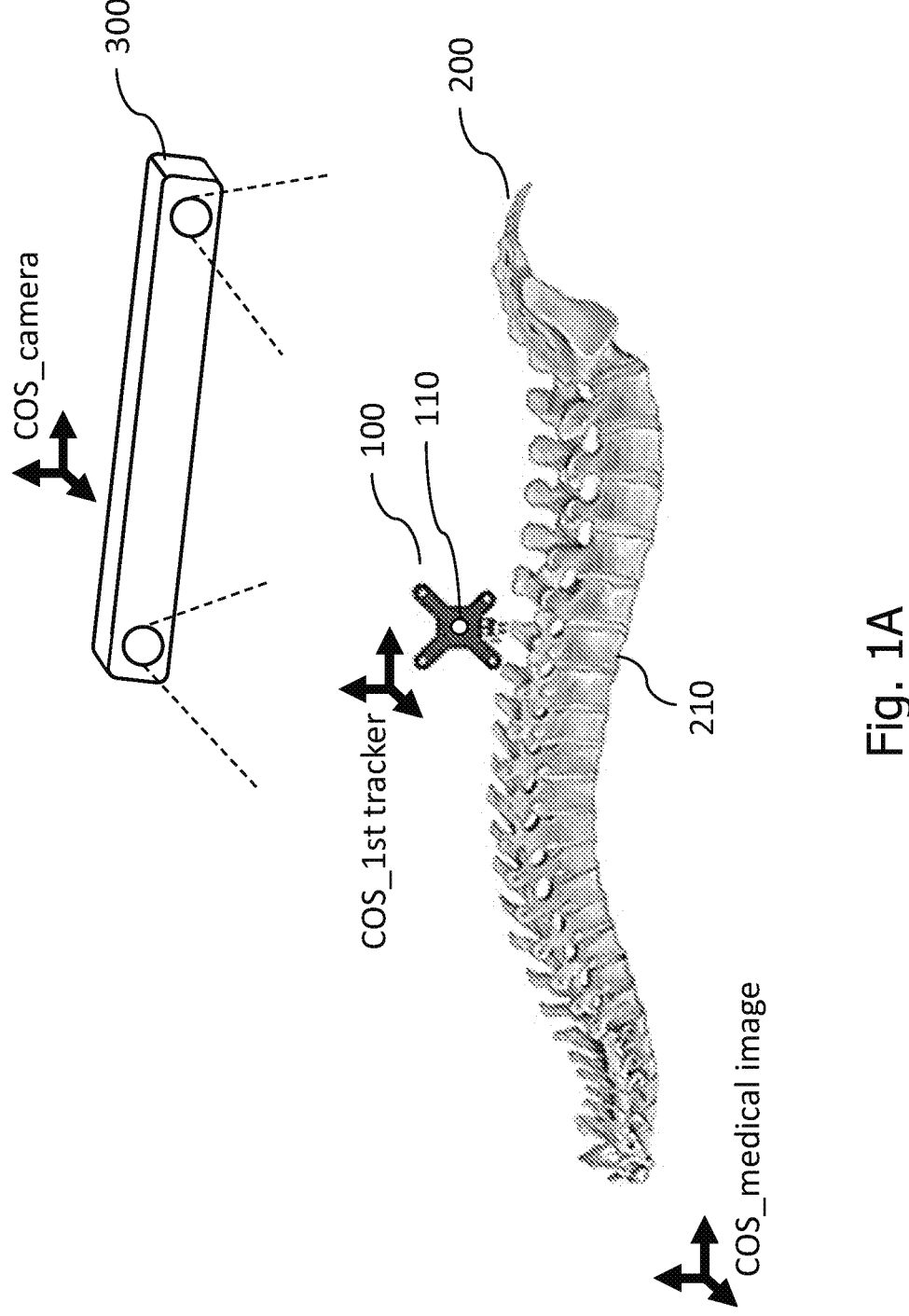
FIG. 1A illustrates a schematic representation of surgical scenario with a patient tracker comprising an acceleration sensor.

In the following description, for purposes of explanation and not limitation, specific details are set forth in order to provide a thorough understanding of the present disclosure. It will be apparent to one skilled in the art that the present disclosure may be practiced in other embodiments that depart from these specific details.

The same reference numerals are used to denote the same or similar components.

FIG. 1A illustrates a schematic representation of surgical tracking scenario with a patient tracker 100 associated with a coordinate system COS_1st tracker and comprising an acceleration sensor 110. The acceleration sensor 110 is configured to generate inertial data indicative of an acceleration of the tracker 100. In some implementations the acceleration sensor 110 comprises at least one of an accelerometer and a gyroscope, e.g., three accelerometers and/or three gyroscopes. In some implementations the inertial data are indicative of acceleration in multiple DOFs (e.g., in at least 3 translatory DOFs and/or in at least 3 rotatory DOFs, or in 6 DOFs in total). The inertial data indicative of acceleration in multiple DOFs are acquired, for example, by a multiple-axes accelerometer or by a combination of multiple single-axis accelerometers. The at least one acceleration sensor 110 may be configured as, or comprised by, an IMU.

The tracker 100 further comprises at least one, e.g., four, passive or active optical markers, e.g., at least one LED. An origin of COS_1st tracker may be selected in a fixed positional relation to the optical markers. It is to be noted that in other embodiments, the tracker 100 may be a non-optical tracker, e.g., an electromagnetic tracker that may comprise one or more coils configured to detect an electromagnetic field as generated by a field generator. In other embodiments, the origin of COS_1st tracker may be selected in a fixed position in relation to, e.g., the acceleration sensor 110 or any distinctly identifiable point of the tracker 100.

The tracker 100 is attached to a portion of a patient anatomy 200, e.g., to a vertebra 210 of the patient's spine. In some variants, the tracker 100 is clamped to a spinal process of the vertebra 210. In other variants, the tracker 100 is configured to be attached (e.g., via an adhesive or otherwise) to a skin surface.

FIG. 1A further illustrates a camera system 300 configured for optically tracking the optical markers of the tracker 100 and generating image data indicative of the tracker 100.

In some variants, the camera system 300 comprises a stereo camera to acquire three-dimensional image data, as indicated in FIG. 1A. The image data indicative of the tracker 100 generated by the camera system 300 is associated with a coordinate system COS_camera. An origin of COS_camera may be selected to lie in a center between the two cameras units of the stereo camera.

Further, two- or three-dimensional medical image data of the patient anatomy 200 is provided. The medical image data are associated with a coordinate system COS_medical image. The medical image data have been previously generated, for example via a medical image modality such as MRI, ultrasound imaging, X-ray projection techniques, angiography or CT. In the example illustrated in FIG. 1A, the medical image data may pertain only to the particular vertebra 210 to which the tracker 100 is attached (e.g., as defined by a bounding box separating the vertebra 210 from neighboring vertebra). In other variants, the medical image data may pertain to multiple vertebrae, including the particular vertebra 210 to which the tracker 100 is attached.

Figures 1B, 1C:
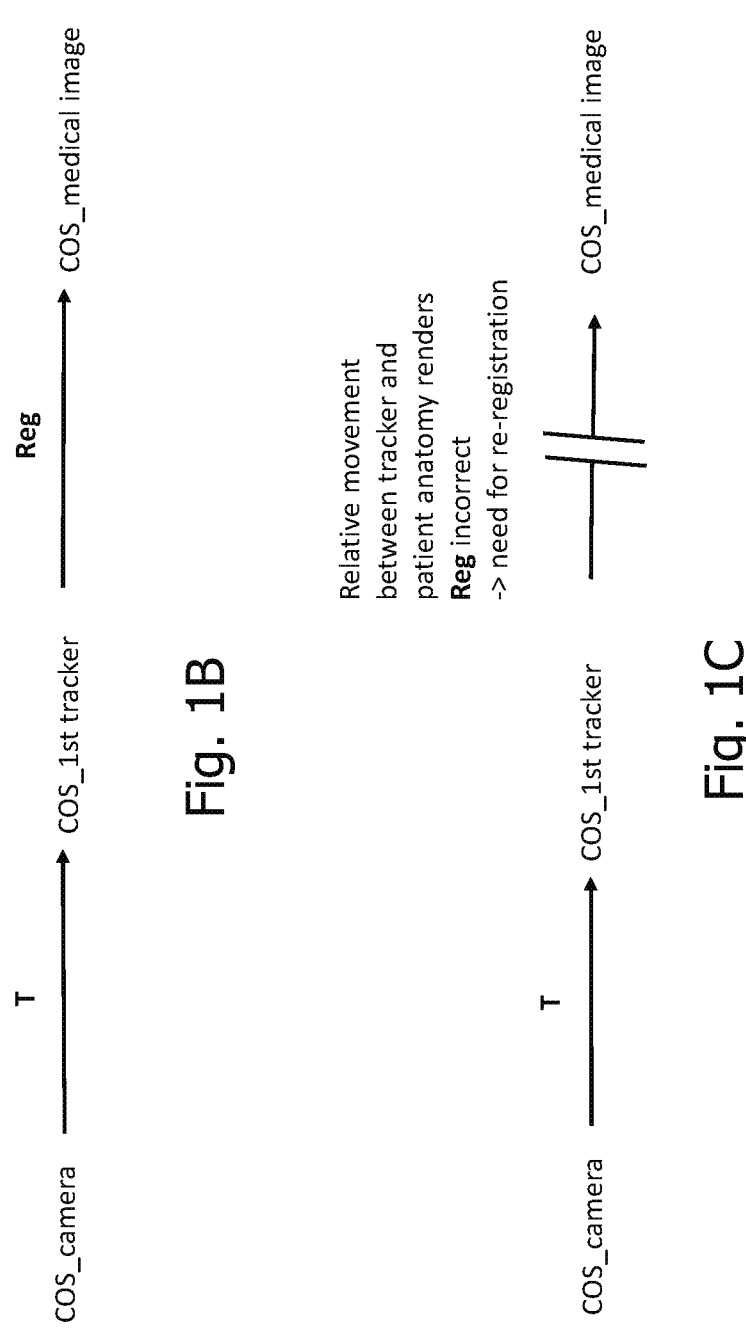
FIG. 1B illustrates a schematic representation of coordinate transformations after an initial registration.
FIG. 1C illustrates a schematic representation of the coordinate transformations of FIG. 1B after a tracker movement relative to the patient anatomy is detected.

FIG. 1B illustrates a schematic representation of coordinate transformations between the three coordinate systems COS_camera COS_1st tracker, and COS_medical image.

The coordinate systems COS_camera and COS_1st tracker are related by a known or at least derivable coordinate transformation T (and its inverse transformation T^−1). The coordinate transformation T is, for example, derivable based on an at least temporarily fixed position between the camera system 300 and the tracker 100. The transformation T may continuously be updated as the patient anatomy 200 with the tracker 100 is moved relative to the camera system 300 in an intentional manner.

Since the coordinate systems COS_1st tracker and COS_camera are related by the transformation T, each of the coordinate systems COS_1st tracker and COS_camera is suited to serve as a first coordinate system in an initial registration process for registering the first coordinate system with the medical image coordinate system COS_medical image. While both coordinate systems are suited to serve as the first coordinate system in the initial registration process, in practice only one registration is needed. In this regard, COS_1st tracker is chosen as the first coordinate system in the following description, as is illustrated in FIG. 1B. The coordinate transformation derived by the initial registration process is denoted Reg, referring to registering of COS_1st tracker with COS_medical image.

The initial registration process may be performed in various ways, for example by touching anatomical features of the vertebra 210 with a tracked pointer tool (not shown) and matching the point cloud thus obtained in COS_camera with corresponding vertebra surface information as detected in the medical image data associated with COS_medical image.

During surgery, there are different kinds of accelerations possibly acting on the tracker 100, and these accelerations are associated with different kinds of movements of the tracker 100. For example, the tracker 100 may be accelerated intentionally, e.g., when a surgeon moves the patient anatomy 200 together with the tracker 100, or when an operating table the patient is lying on is moved. Further, the tracker 100 may be accelerated due to a positional drift of the tracker, e.g., as the tracker 100 is clamped to the patient and a clamping force is not sufficient to fixedly attach the tracker 100 to the patient over an extended period of time in view of gravitational forces acting on the tracker. Still further, the tracker 100 may unintentionally be bumped against by a surgeon or a robot, i.e., there may be an acceleration due to an impact on the tracker 100.

These or other tracker accelerations may lead to a relative movement between the tracker 100 and the patient anatomy 200, in particular the vertebra 210 the tracker 100 is attached to. As a result, the initial registration Reg is rendered incorrect and a re-registration of COS_1st tracker with COS_medical image is necessary (e.g., for ensuring correct navigation of a tracked surgical tool by a surgeon or robot). A schematic representation of this case is illustrated in FIG. 1C.

Figure 1D:
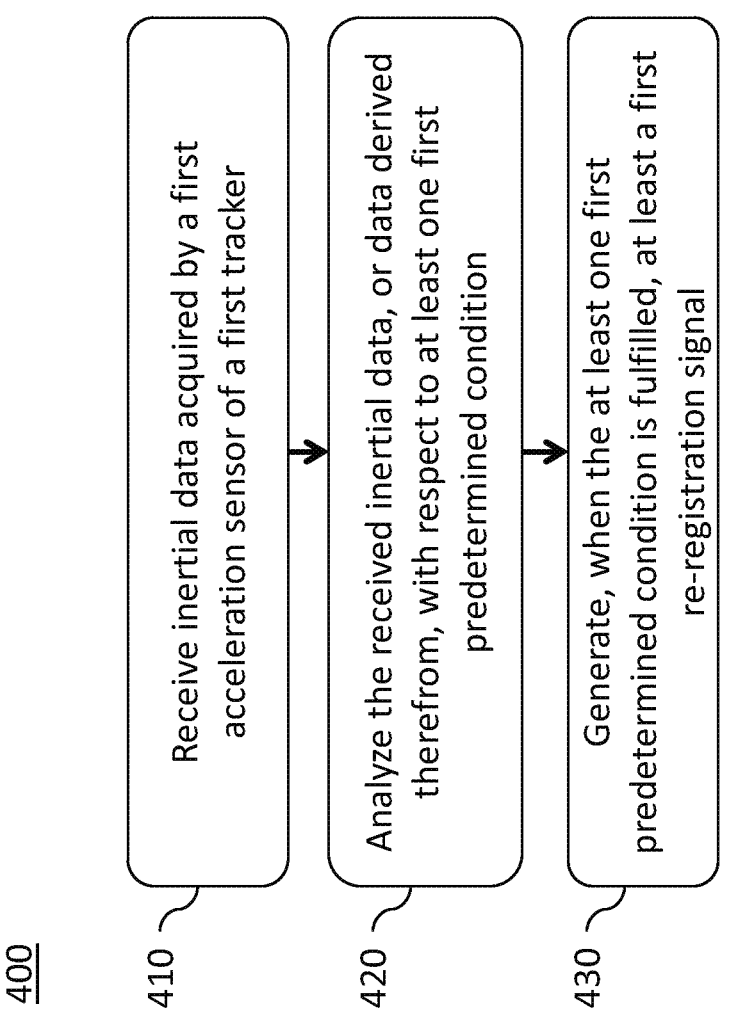
FIG. 1D illustrates a flow diagram of a method for detecting a need of re-registration for a patient tracker.

FIG. 1D illustrates a flow diagram 400 of a method for determining a need for a re-registration of the tracker 100 as attached to the patient anatomy 200.

The method comprises a step 410 of receiving inertial data acquired by the acceleration sensor 110 of the tracker 100. The inertial data may be acquired in one or more DOFs. The inertial data may be sensor data as generated by the acceleration sensor 110.

In step 420, the received inertial data, or data derived therefrom (e.g., by one or more processing operations), is analyzed with respect to at least one first predetermined condition. The at least one first predetermined condition can be associated with one or different kinds of acceleration of the tracker 100, e.g., a drift of the tracker 100 or an impact on the tracker 100. For example, an impact on the tracker 100 can be associated with the inertial data being indicative of an acceleration exceeding an acceleration threshold, e.g., of at least 5 m/s$^2$ or higher. In another example, an impact on the tracker 100 may be associated with an acceleration indicative of a predefined movement over time, e.g., a damped oscillation having a certain behavior as defined by the at least one first predetermined condition.

Figure 1F:
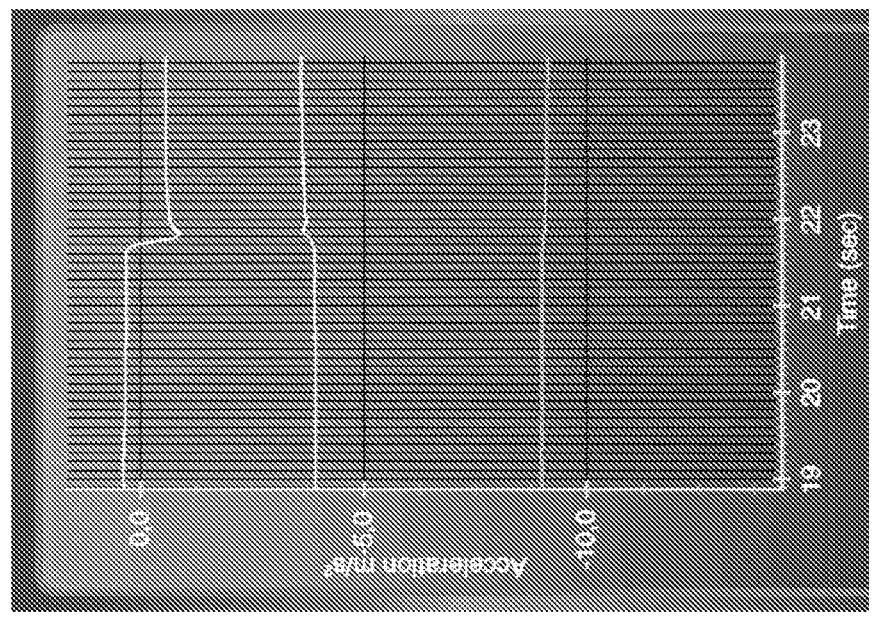
FIGS. 1E, 1F illustrate schematic representations of inertial data acquired by an acceleration sensor.
Figure 1E:
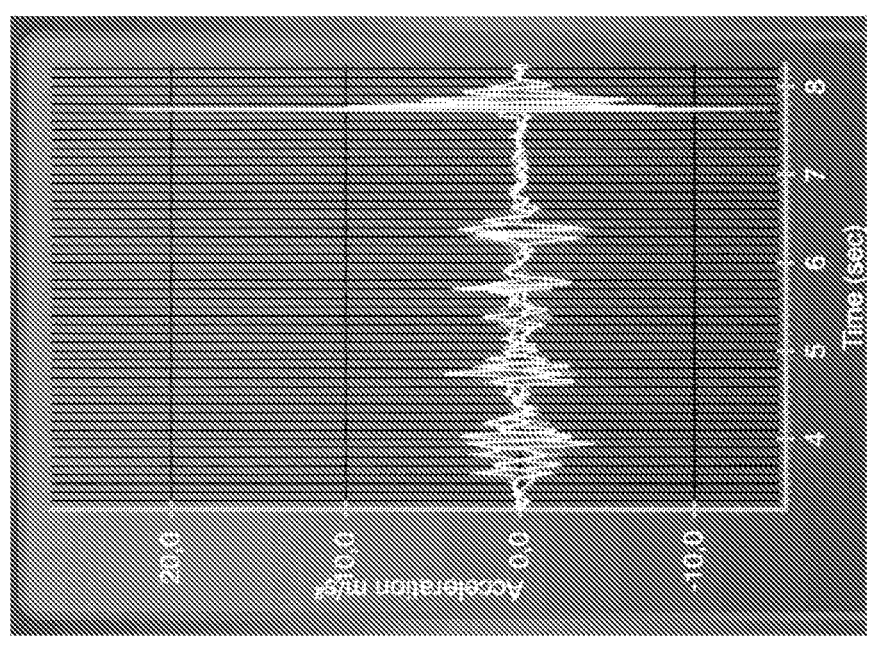

Exemplary inertial data acquired by one or more acceleration sensors 110 comprised by an IMU are illustrated in FIGS. 1E and 1F. The IMU typically comprises multiple acceleration sensors 110 aligned with different axes and indicative of different DOFs. Each accelerometer and gyroscope generates inertial data that can be received and analyzed. While only one accelerometer or gyroscope may be necessary for determining a need for re-registration as described herein, receiving inertial data from multiple such sources may improve the accuracy of determining a need of a re-registration.

FIG. 1E shows an acceleration in m/s$^2$ of the tracker 100 as a function of time in s for three separate acceleration sensors 110 (here: accelerometers) supported by the tracker 100 and aligned with different axis. In the shown example, multiple movements of the tracker 100 can be identified in the inertial data. Before second 7, all detected accelerations are below an acceleration threshold of, for example, 5 m/s$^2$ (or higher). These accelerations may be associated with controlled movements or at least with movements not indicating an impact on the tracker 100, that would give rise to a need for a re-registration. The acceleration beginning at 7.8 seconds shows a damped oscillation with an initial acceleration peak of over 20 m/s$^2$. As such, the acceleration threshold of 5 m/s$^2$ is exceeded, which indicates an impact on the tracker 100 and possibly a need for a re-registration. Such a need may alternatively, or additionally, be derived from the damped oscillation behavior of the signals illustrated in FIG. 1E. Regarding the example data shown in FIG. 1E, it is to be noted that the data was standardized by subtracting a gravitational acceleration from the data.

FIG. 1F shows three independent measurements as determined by three acceleration sensors 110 for three different DOFs (in m/s$^2$ as a function of time in s). The shown measurements are indicative of a gravity vector G in the position of the tracker 100. In case the position of the tracker 100 changes, the measured acceleration indicative of the gravity vector G also changes. Such behavior can be seen at a time of around 21.5 to 22 seconds. Here the measured gravity vector changes and does not return to its initial value, which indicates a permanent positional change of the accelerometers of acceleration sensor 110, i.e., of the tracker 100. Therefore, a change of the acceleration indicative of the gravity vector G may form the basis of another, or alternative, predetermined condition indicative of a need for a re-registration (e.g., of drift of the tracker 100 or an impact on the tracker 100).

Returning to FIG. 1D, in step 430, in case the at least one first predetermined condition is fulfilled, i.e., in case a need for re-registration of the tracker 100 is determined, at least one re-registration signal is generated. The at least one re-registration signal may trigger a re-registration notification. In one variant, the re-registration notification may be indicative of a need for a re-registration. The re-registration notification may be, or may trigger, a user notification suggesting triggering of the re-registration to a user. In another variant, the registration notification may be indicative of a re-registration that is triggered automatically. The automatically triggered re-registration may be a re-registration of COS_1st tracker with COS_medical image.

Figure 1G:
FIG. 1G illustrates a schematic representation of the coordinate transformations of FIG. 1C after a re-registration.

When the re-registration is triggered automatically or manually, new coordinate transformations for the re-registration are determined (e.g., in a similar manner as for the initial registration). FIG. 1G illustrates a schematic representation of coordinate transformations between the three coordinate systems COS_camera, COS_1st tracker and COS_medical image comprising the re-registration denoted as Re_Reg, determined analogous to the initial registrations Reg shown in FIG. 1B.

Figure 2A:
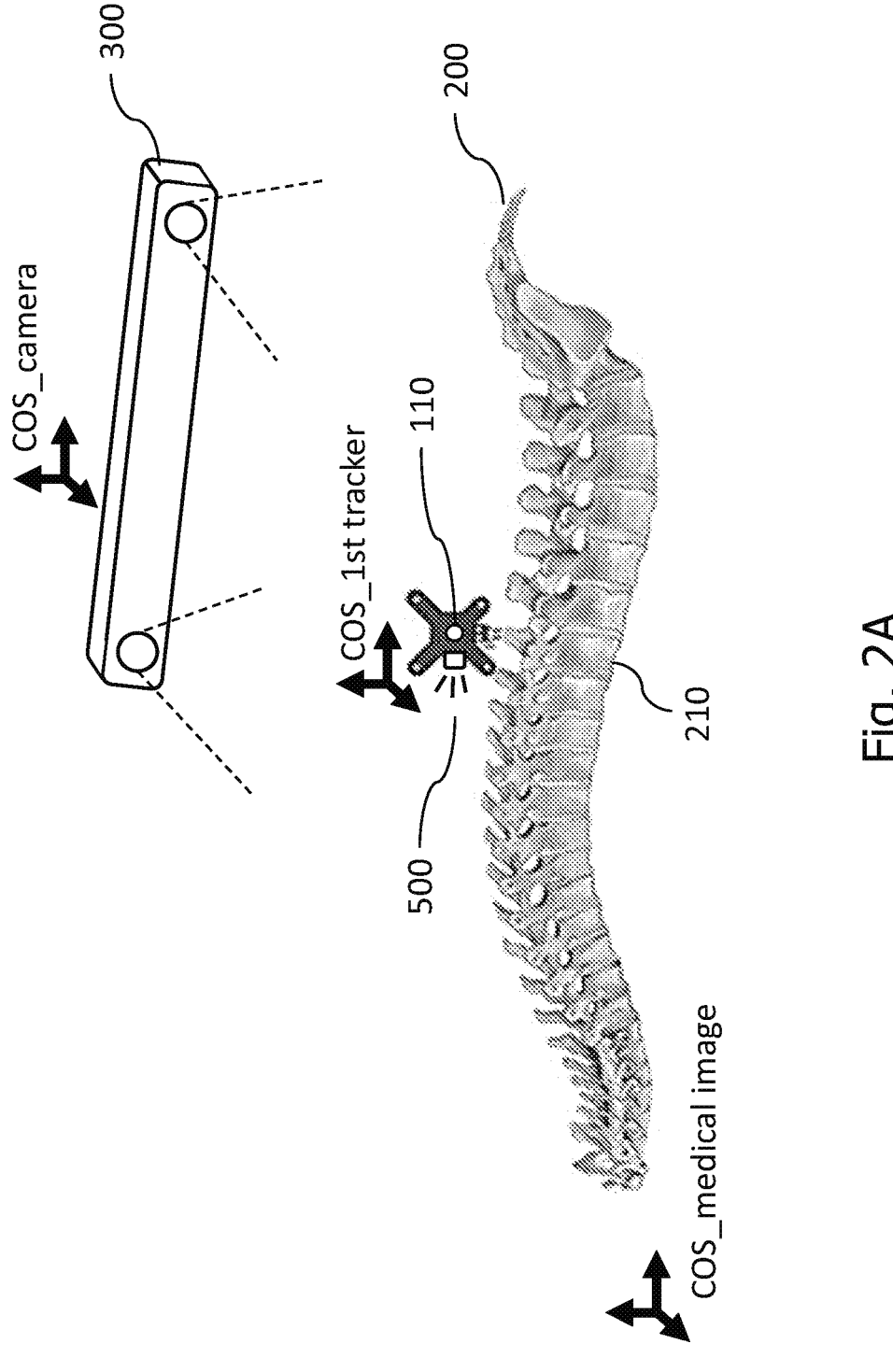
FIG. 2A illustrates the schematic representation of the surgical scenario shown in FIG. 1A with the patient tracker additionally comprising a notification device.

FIG. 2A illustrates the surgical scenario of FIG. 1A with the patient tracker 100 additionally comprising a notification device 500 as an integral part thereof. The shown notification device 500 is an optical device, e.g., a LED or a LED configuration comprising multiple LEDs.

The notification device 500 is configured to output, responsive to the re-registration signal, a notification signal. The notification signal may be a re-registration notification for notifying a user that a re-registration has been triggered automatically or that a need for a re-registration has been determined. The notification signal may be generated by switching an LED to a different mode, e.g., to a different color (e.g., from green to red), to a different geometric pattern in case of multiple LEDs (e.g., from a ring to a cross) or to a different operating frequency (e.g., from constant illumination to an on/off modulation at 1 to 10 Hz).

Figure 2C:
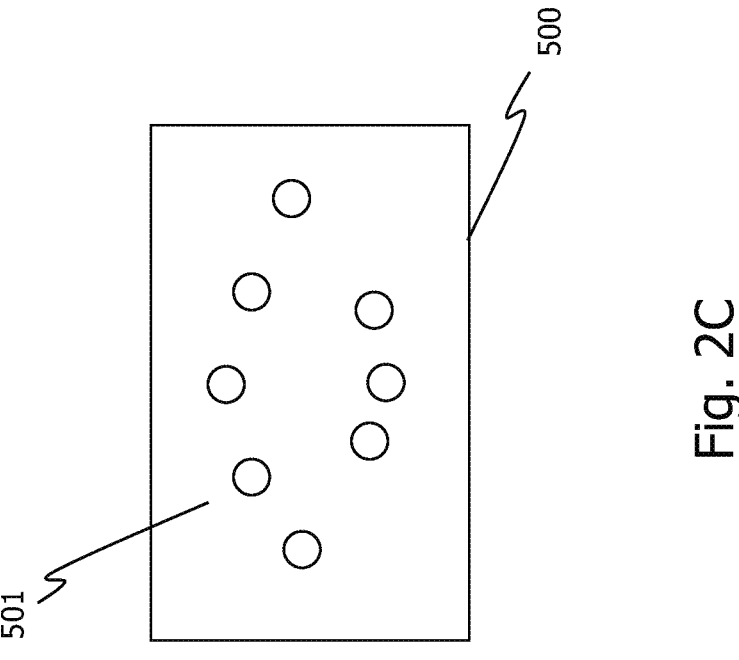
FIG. 2C illustrates a schematic representation of multiple tracker LEDs showing a second lighting pattern.
Figure 2B:
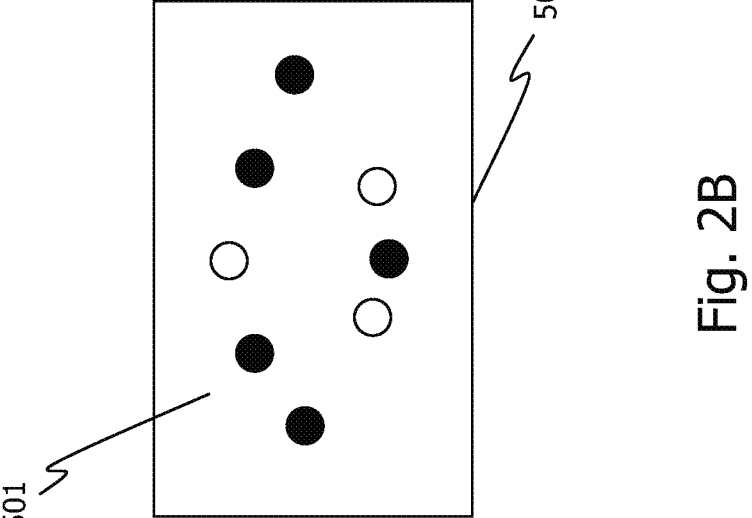
FIG. 2B illustrates a schematic representation of multiple tracker LEDs showing a first lighting pattern.

An example of a notification device 500 with multiple LEDs 501 switching from a first geometric pattern to a second geometric pattern is illustrated in FIGS. 2B and 2C. In FIG. 2B only three of the shown LEDs 501 emit light (displayed as a black circle with a white filling). In FIG. 2C, all of the LEDs 501 emit light.

In other examples (not shown), the notification device 500 is an acoustic device (e.g., a loudspeaker) or a combination of an optical and an acoustical device 500. Accordingly, the user notification signal that is output by the notification device 500 may be an optic or acoustic notification or a combination thereof.

Figure 2D:
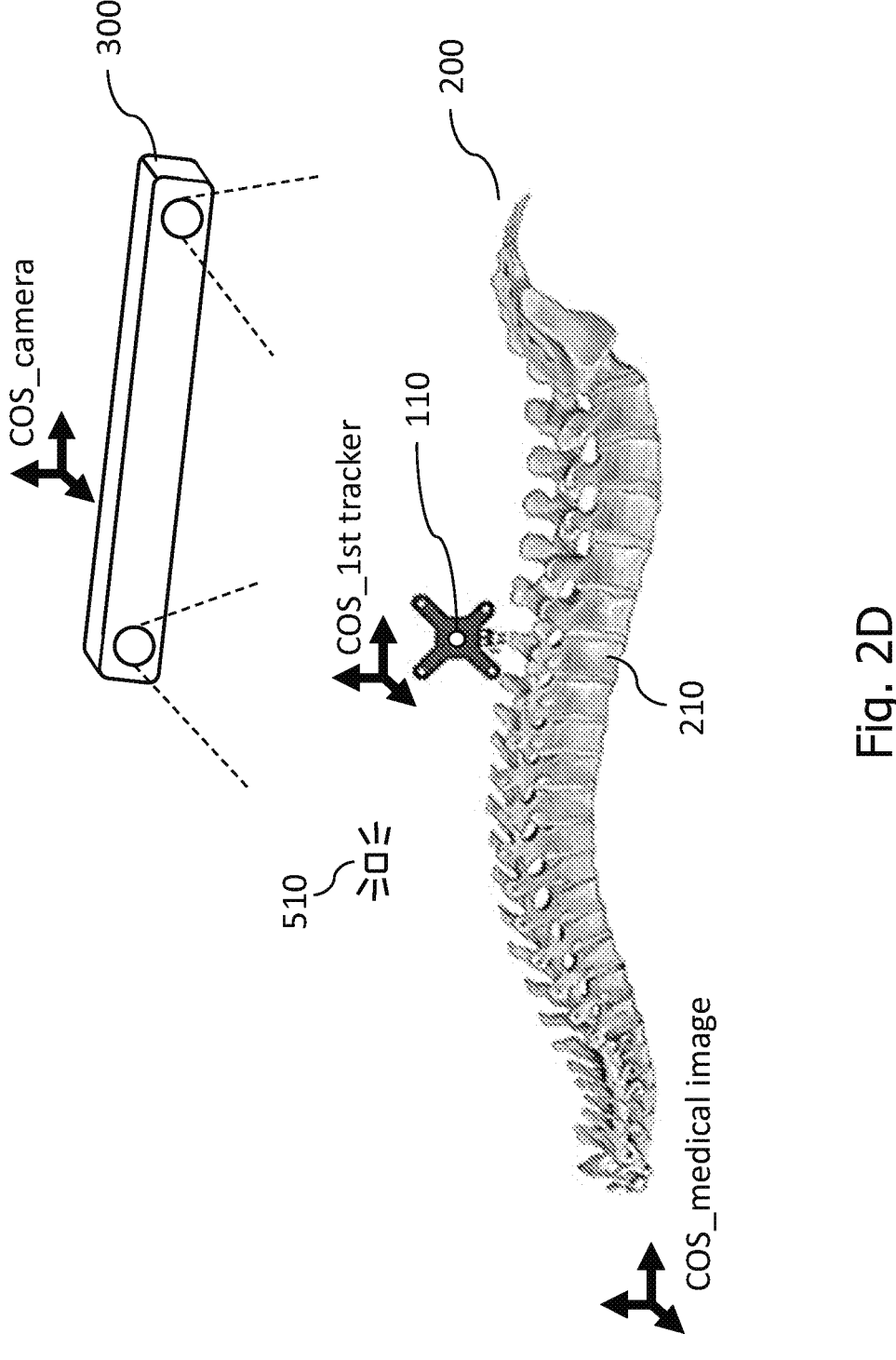
FIG. 2D illustrates a schematic representation of the surgical scenario shown in FIG. 1A with a separate notification device.

FIG. 2D illustrates the surgical scenario of FIG. 1A with a notification device 510 that is separate from the patient tracker 100. The separate notification device 510 may in some variants be provided in addition to the integral notification device 500 of FIG. 2A. In the example of FIG. 2D, the separate notification device 510 is provided as an alternative to the integral notification device 500.

The notification device 510 may be an optical or acoustical notification device or a combination thereof, analogous to the notification device 500 comprised by the patient tracker 100. The notification device 510 has a similar functionality as the notification device 500 of FIG. 2A. The notification device 510 shown in FIG. 2D is a standalone device 510 that is in (e.g., wireless) communication with the tracker 100 to receive the re-registration signal. As possible examples of wireless communication, the notification device 510 is configured to receive the re-registration signal via radio frequency (RF) communication (using, e.g., Bluetooth technology) or via infrared (IR) communication.

Figure 2E:
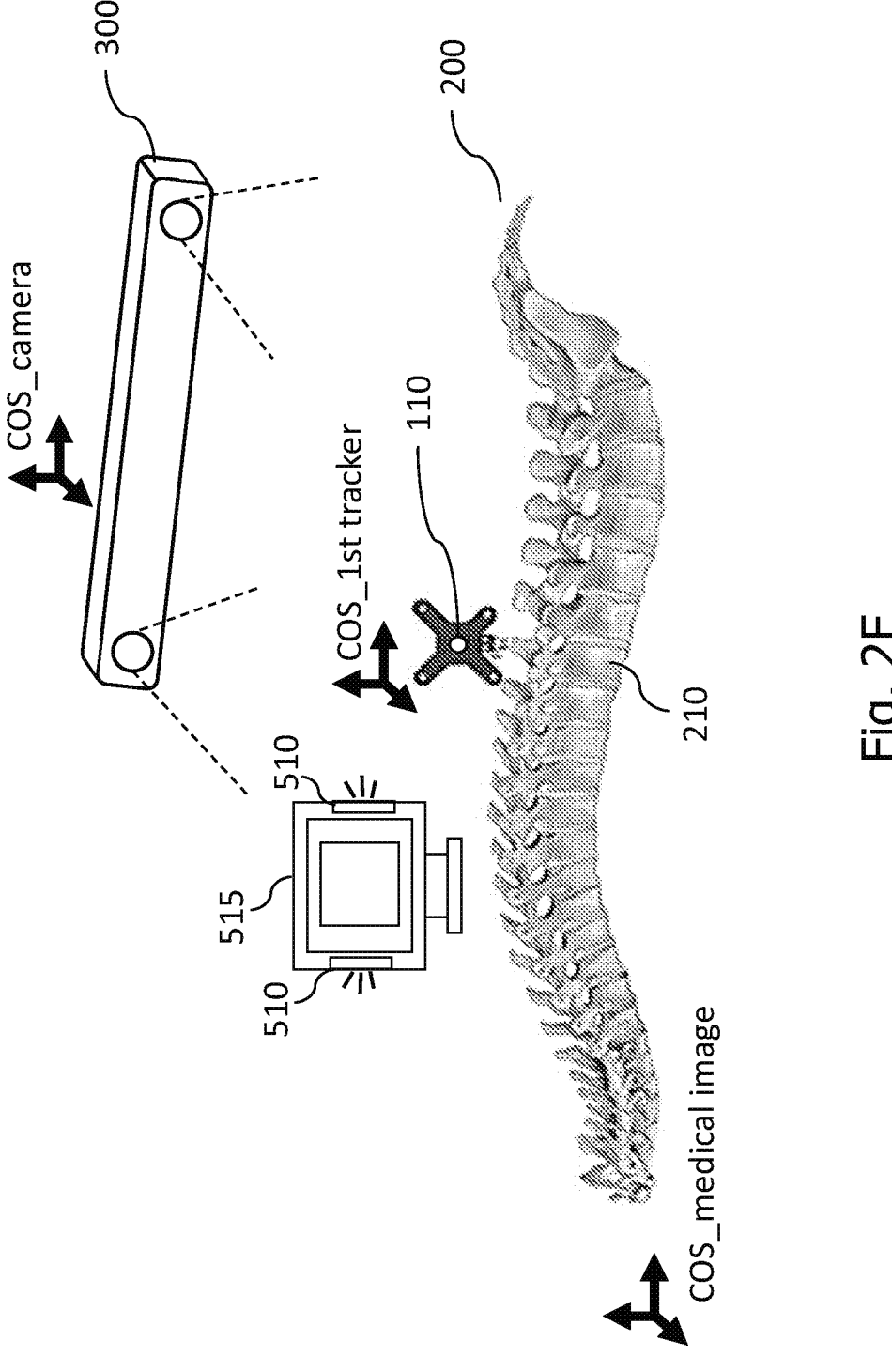
FIG. 2E illustrates another schematic representation of the surgical scenario shown in FIG. 1A with a separate notification device.

FIG. 2E illustrates the surgical scenario of FIG. 1A with another implementation of the notification device 510 that is separate from the tracker 100. The notification device 510 shown in FIG. 2E is comprised by a computing system 515 that is in communication with the patient tracker 100 to (e.g., wirelessly) receive the re-registration signal. The notification device 510 has a similar functionality as the notification device 500 of FIG. 2A. The computing system 515 comprises a display and is configured to generate a pop-up window as notification signal. The separate notification device 510 may further be configured to generate a sound when the pop-up window is generated.

Figure 2F:
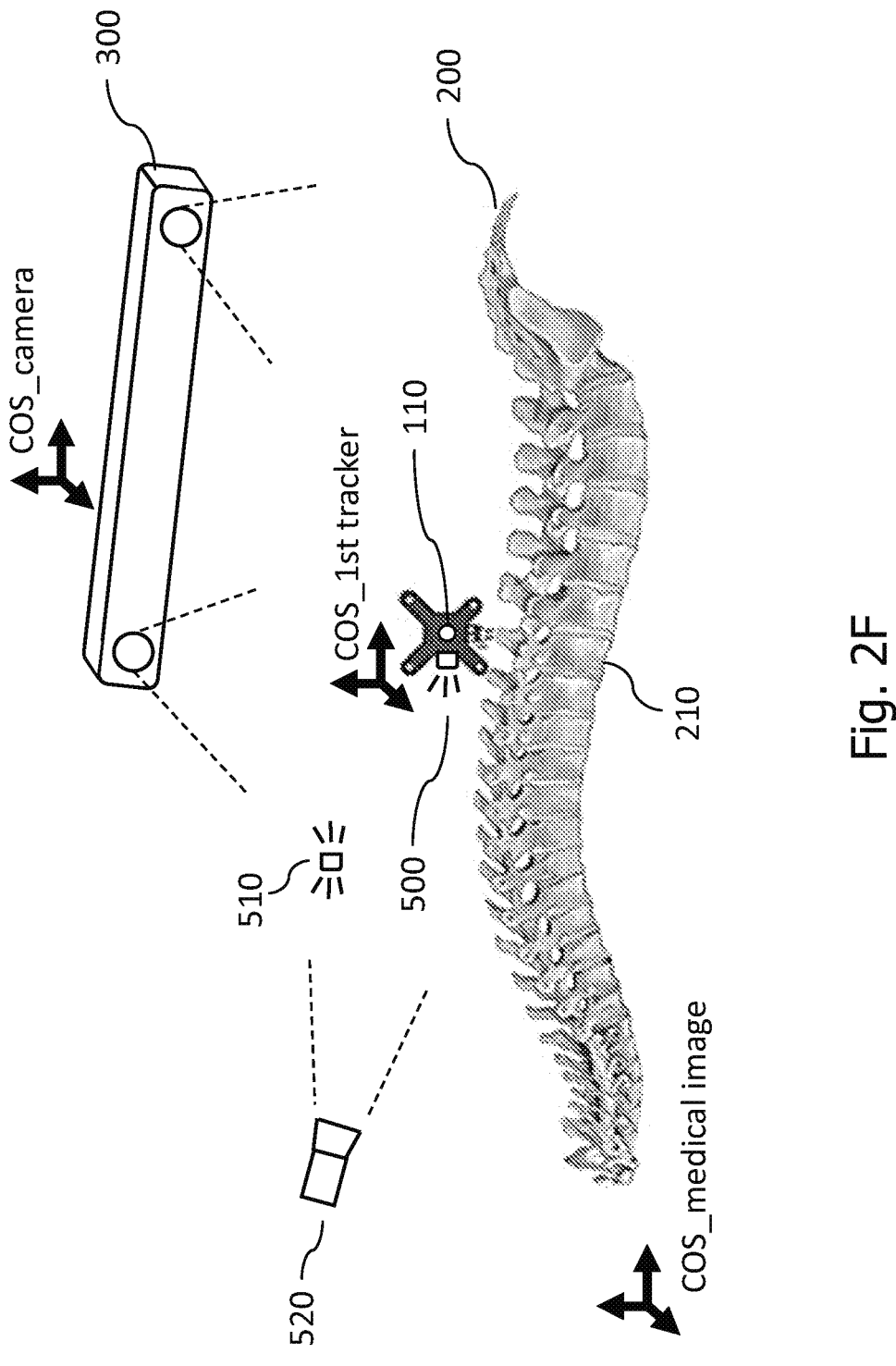
FIG. 2F illustrates a schematic representation of a combination of the scenarios of FIGS. 2A and 2B with a separate monitoring device.

FIG. 2F illustrates a combination of the surgical scenarios of FIGS. 2A and 2D with an additional separate monitoring device 520. One or both of the notification devices 500, 510 are monitored by at least one of the camera system 300 and the separate monitoring device 520. The separate monitoring device 520 may comprise at least one of a camera, a microphone, an IR-receiver and a radio frequency receiver (e.g., a Bluetooth receiver).

In this variant, the re-registration signal is configured to trigger the re-registration notification to one or both of the separate monitoring device 520 and the camera system 300. Upon detecting of the re-registration notification, a second re-registration signal is generated. The second re-registration signal is configured to trigger an automatic re-registration of COS_1st tracker with COS_medical image. Alternatively the second re-registration signal triggers an automatic user notification suggesting to a user to trigger the re-registration.

Figure 2G:
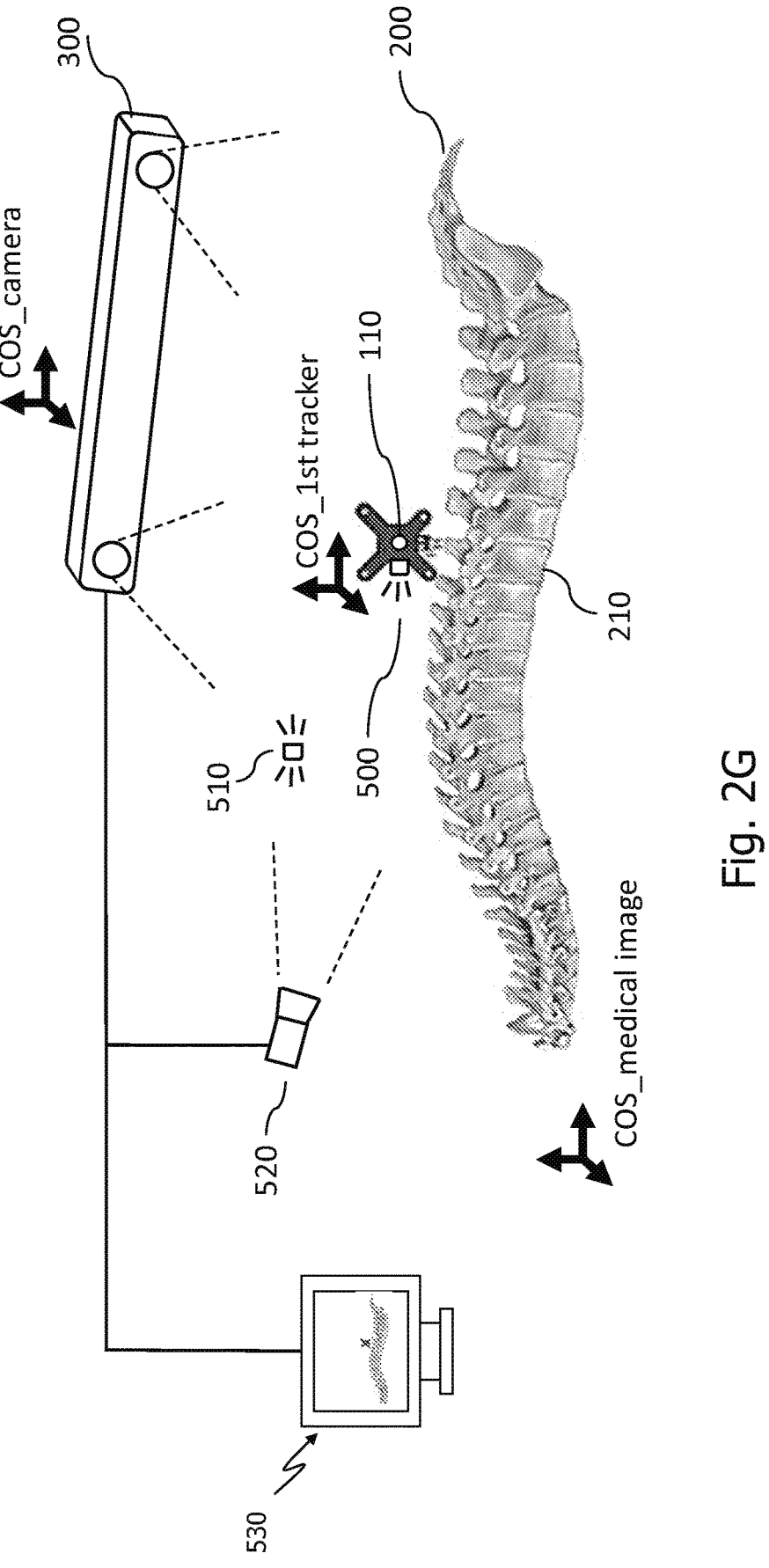
FIG. 2G illustrates a schematic representation of a system for visualizing image data.

FIG. 2G illustrates a schematic representation of a system for visualizing image data representative of the patient tracker 100 and its environment. The image data to be visualized is generated by at least one of the camera system 300, the monitoring device 520 and separate camera (not shown) that continuously images the tracker 100.

The image data thus obtained is intended to be visualized, e.g., on a display 530, in the field of view of a user. The image data is, for example, continuously stored in a ring buffer of a certain size (e.g., sufficient to store at least 10 seconds of image data). The image data is configured to be replayed when an unintended movement of the patient tracker 100 (in particular an impact) is detected. In some examples, the image data is visualized in response to a manual input of a user (e.g., in response to the notification being output by the notification device 500) or automatically. The visualization of the image data may help a user identifying the kind of detected tracker movement and deciding whether or not a re-registration is necessary. The visualization may reduce cognitive load on a surgeon and duration of a surgery.

Figure 3A:
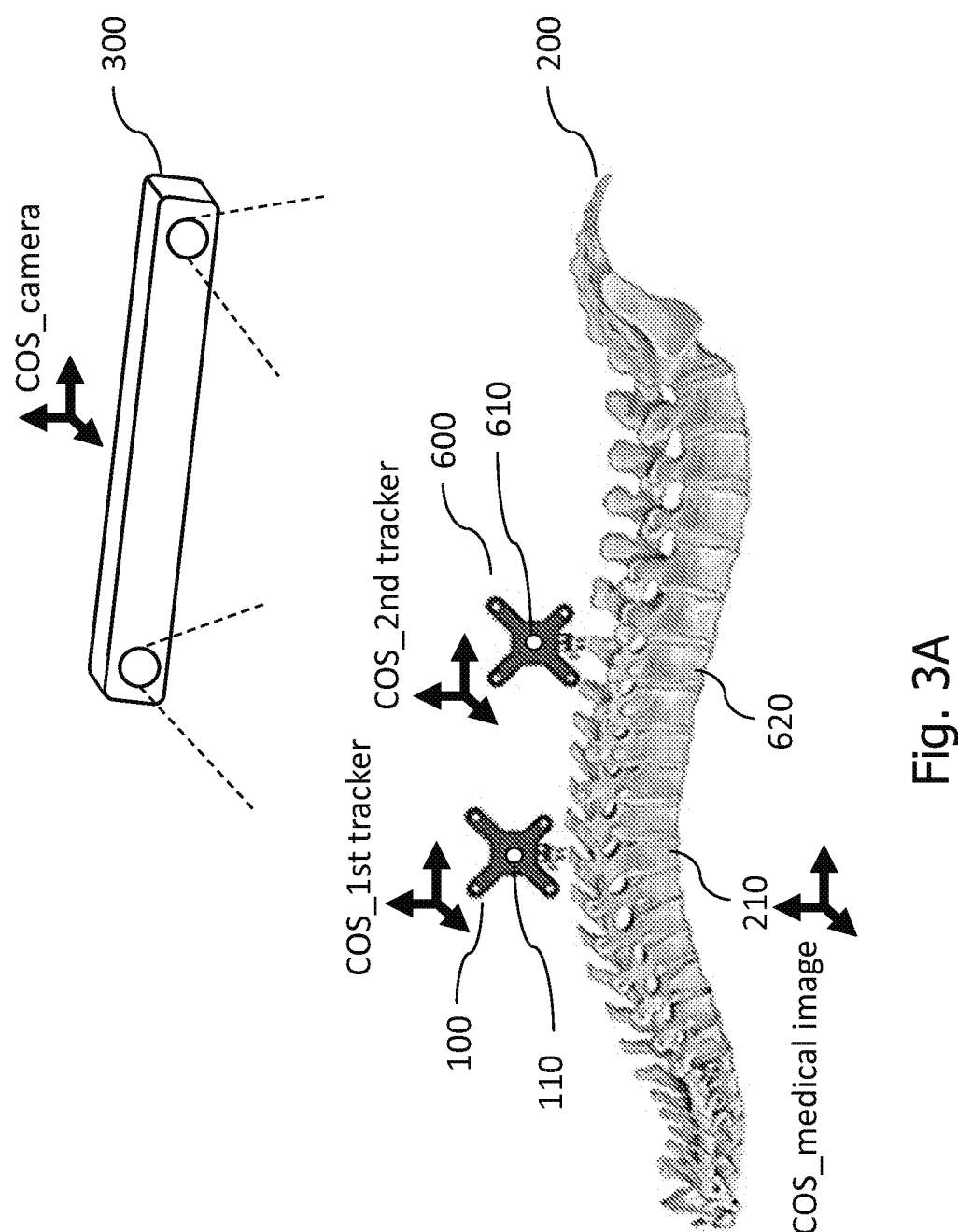
FIG. 3A illustrates a schematic representation of the surgical scenario of FIG. 1A with an additional second tracker comprising a second acceleration sensor.

FIG. 3A illustrates the surgical scenario of FIG. 1A with an additional second patient tracker 600 associated with a coordinate system COS_2nd tracker. Similar to the first patient tracker 100, the second patient tracker 600 comprises a second acceleration sensor 610. The second acceleration sensor 610 is configured to acquire inertial data indicative of an acceleration of the second tracker 600, analogous to the first acceleration sensor 110 of the first tracker 100.

The first tracker 100 and the second tracker 600 are attached to different vertebra 210, 620 of the patient anatomy 200. Again, the camera system 300 is provided for optically tracking the first tracker 100 and the second tracker 600. The image data of the second tracker 600 generated by the camera system 300 are also associated with the camera coordinate system COS_camera.

Medical image data of the vertebrae 210, 620 to which the first tracker 100 and the second tracker 600 are attached are associated with coordinate system COS_medical image. In this example, both vertebrae 210, 620 are associated with the same image medical image data.

The coordinate transformations between COS_1st tracker, COS_camera and COS_medical image as described with reference to FIGS. 1B, 1C and 1G may be analogously defined for the coordinate systems COS_2nd tracker, COS_camera and COS_medical image. An initial registration between between COS_2nd tracker and COS_medical image is denoted as Reg_2 in the following. Since COS_camera is related to both COS_1st tracker and COS_2nd tracker, a coordinate transformation T_tracker (and its inverse transformation T_tracker^−1) between the two tracker coordinate systems COS_1st tracker and COS_2nd tracker is derivable.

FIG. 3B illustrates a flow diagram 700 of a method variant for determining a need for a re-registration of the patient tracker 100 attached to the patient anatomy 200. The three steps 710, 720, and 730 are performed analogously to the method described with reference to FIG. 1D, i.e., receiving and analyzing inertial data from the first acceleration sensor 110 and generating a first re-registration signal, when the at least one first predetermined condition is fulfilled, except for a possible modification of step 730 compared to step 430.

At this point the first re-registration signal could trigger, or may suggest to a user, a re-registration similar to the initial registration. However, such a re-registration is still time consuming and consumes computational power. To reduce the required amount of time and computational power, the re-registration is based on the known registration Reg_2 of the second tracker 600. Therefore, prior to triggering, or suggesting, a re-registration via any re-registration signal (e.g., the first re-registration signal or the second re-registration signal as described with reference to FIG. 2F), inertial data from the second acceleration sensor 610 is received in step 740.

In step 750, the inertial data received from the second acceleration sensor 610, or data derived therefrom, are analyzed with respect to at least one second predetermined condition indicative of a drift of the second tracker 600 or an impact on the second tracker 600. The second predetermined condition may be the same as the first predetermined condition (e.g., as explained above with reference to step 420 of FIG. 1D) or different therefrom. Steps 710 and 720 as well as steps 740 and 750 may be performed substantially in parallel, as indicated in FIG. 3B.

In step 760, if the at least one second predetermined condition is not fulfilled (i.e., if Reg_2 is still considered to be correct) while the first predetermined condition is fulfilled, a re-registration of COS_1st tracker with COS_medical image based on Reg_2 and T_Tracker is automatically executed, or is suggested to a user, via the re-registration signal generated in step 730. In some variants, step 730 may thus be integrated in step 760 (i.e., be a sub-step thereof).

Thus, as long as a need for re-registration is determined for only one of the first tracker 100 and second tracker 600, a re-registration of a coordinate system associated with the respective tracker 100, 600 can be performed based on the registration of the coordinate system associated with the other one of the first and second tracker 100, 600.

Figure 4A:
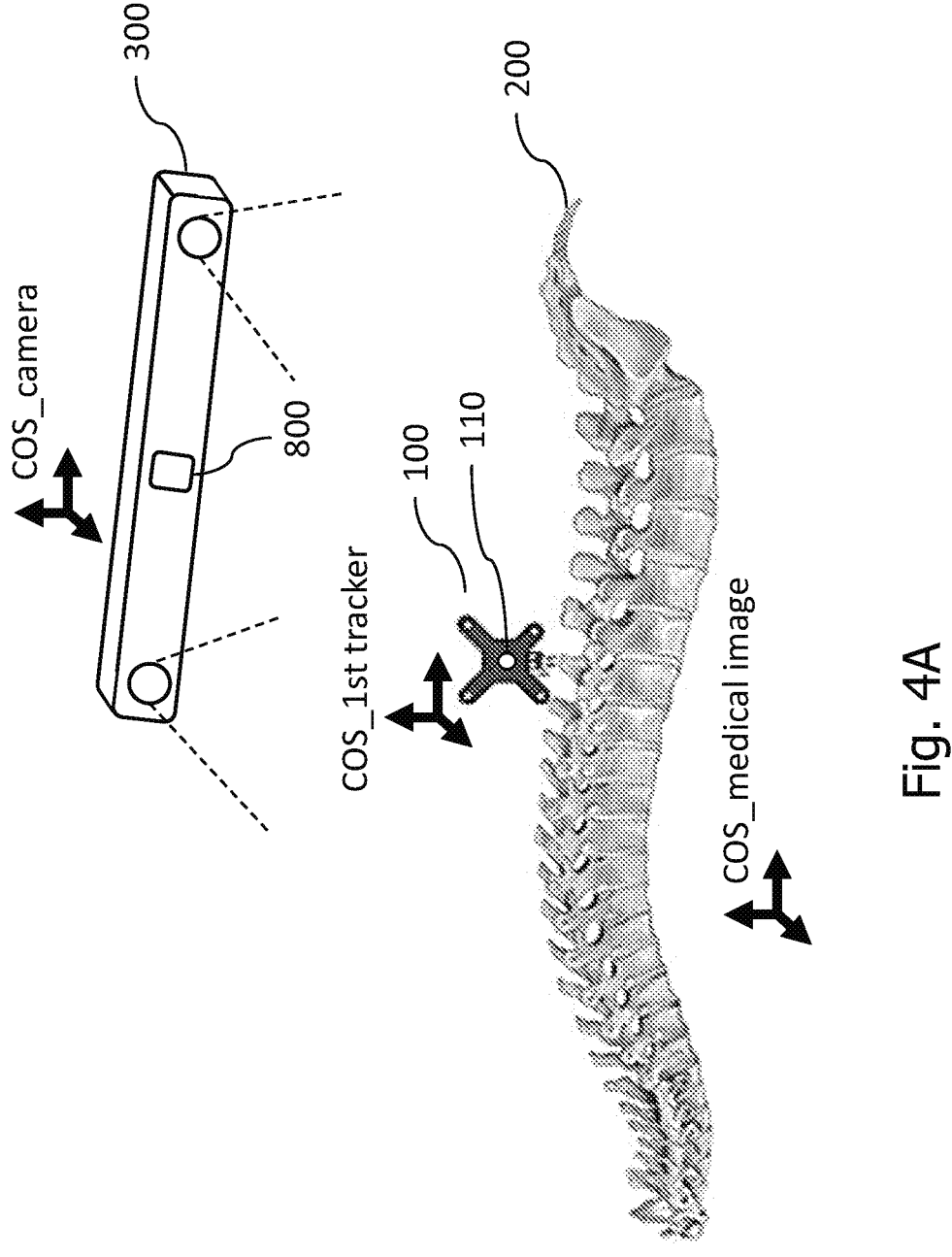
FIG. 4A illustrates a schematic representation of the surgical scenario shown in FIG. 1A with a camera system comprising an acceleration sensor.
Figure 4B:
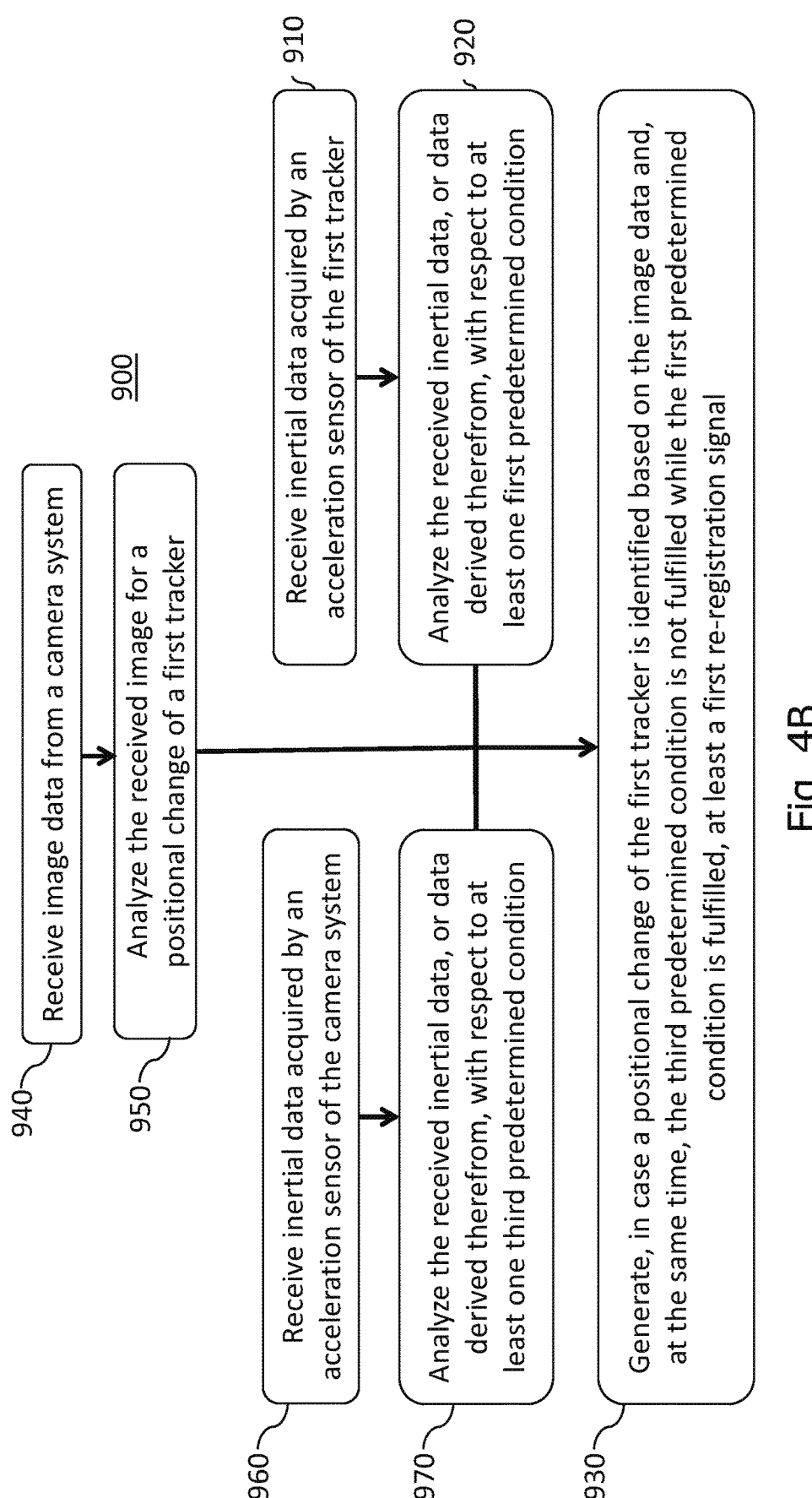
FIG. 4B illustrates a flow diagram of still another variant of the method for detecting a need of re-registration for a patient tracker.

FIG. 4A illustrates a schematic representation of the surgical scenario of FIG. 1A with the camera system 300 comprising a dedicated acceleration sensor 800. The acceleration sensor 800 is configured to generate inertial data indicative of an acceleration of the camera system 300. In this variant, a need for re-registration of the patient tracker 100 may be determined based on the image data generated by the camera system 300 in combination with the inertial data of the third acceleration sensor 800. FIG. 4B illustrates a flow diagram 900 of a corresponding method variant for determining a need for a re-registration of the tracker 100.

In the variant of FIG. 4B, the three steps 910, 920, and 930 are performed analogously to the method described with reference to FIG. 1D, i.e., receiving and analyzing inertial data from the acceleration sensor 110 and generating a re-registration signal when the at least one first predetermined condition is fulfilled, except for a possible modification of step 930 compared to step 430. At this point, or at a later point in time, the re-registration signal may trigger at least one of a re-registration notification and an automatic re-registration, or a suggestion of a re-registration, similar to the re-registration signal described with reference to FIG. 1D.

To increase the accuracy of the determination of the need for a re-registration, the method further comprises a step 940 of receiving image data generated by the camera system 300 and a step 950 of analyzing the received image data for a positional change of the tracker 100, i.e., for a relative movement between the tracker 100 and the camera system 300.

Analyzing the received image data for a positional change of the tracker 100 may comprise determining first and second pixel coordinates of a center of at least one of the tracker 100 and each of the one or more markers of the tracker 100. The first pixel coordinates may be determined from image data taken in a situation without any movement of the tracker 100 or the camera system 300, e.g., directly after the initial registration process. The second pixel coordinates may be determined from the image data received in step 410. A difference between the first and second pixel coordinates may be indicative of a positional change of the tracker 100. Based on the the amount of the difference and/or the duration in which the indicated positional change takes place, the positional change of the tracker 100 may be indicative of at least one of a drift of the tracker and an impact on the tracker 100.

Regarding the camera image data analysis, it has been observed that movement of the tracker 100 and movement of the camera system 300 may result in similar image data changes (i.e., it cannot be told from the image data if the tracker 100 has moved relative to the camera system 300 or vice versa). To address this ambiguity, at least the inertial data generated by the third acceleration sensor 800 is received in step 960.

The received data, or data derived therefrom, are analyzed in step 970 with respect to at least one further predetermined condition indicative of an impact on the camera system 300.

The at least one further predetermined condition indicative of an impact on the camera system 300 may be analogous to the at least one predetermined condition indicative of an impact on the tracker 100 as explained with reference to FIG. 1D above (or it may be different therefrom). Steps 910 and 920, steps 940 and 950 as well as steps 960 and 970 may be performed substantially in parallel, as indicated in FIG. 4B.

Analyzing inertial data of both, the tracker acceleration sensor 110 and the camera system acceleration sensor 800 further enables distinguishing between a movement of the tracker 100, a movement of the camera system 300, and a movement of both of the tracker 100 and the camera system 300. In case a movement of the tracker 100 is identified based on the image data and, at the same time, the inertial data generated by the acceleration sensor 800 is not indicative of an impact on the camera system 300 while the first predetermined condition is fulfilled (see step 920), the at least one re-registration signal is generated in step 930.

In some implementations, the first re-registration signal is generated in case a positional change of the tracker 100 is identified based on the camera image data while the first predetermined condition is fulfilled.

In some implementations, the first re-registration signal is generated in case the inertial data generated by the third acceleration sensor 800 is not indicative of an impact on the camera system 300 while the first predetermined condition is fulfilled.

In one variant, the re-registration signal generated in step 930 triggers generation of a re-registration notification for further facilitating decision-making of a surgeon, e.g., regarding the need of a suggested re-registration of the tracker 100, i.e., of COS_1st tracker with COS_medical image.

By combining an optical data-based determination and an inertial data-based determination as described above, the accuracy of the determination of the need for a re-registration may be increased since the optical data-based determination may be utilized to compensate for possible deficits of the inertial data-based determination and vice versa. For example, a determination based on optical tracking requires a line of sight from the camera system 300 to the tracker 100, 600. A determination based on inertial data on the other hand is applicable without the need for any line of sight. As another example, any inertial data generated by an acceleration sensor 110, 610, 800 is subject to integration drift, as explained above. Image data generated by a camera system 300 on the other hand are only subject to a positional drift of the camera system 300 or the tracker 100, 600.

Data generated by the camera system 300 and any of the acceleration sensors 110, 610, 800 as described above may be received in near real time. The generated data from the camera system 300 and any or all of the acceleration sensors 110, 610, 800 may be received substantially in parallel. Alternatively, some or all of the generated data may be received in sequence. For example, the inertial data from the third acceleration sensor 800 may only be received when a positional change of the first tracker 100 is indicated in the received image data. In this case, the inertial data may be associated with the corresponding image data based on time stamps. As a result, usage of energy and data transmitting resources may be reduced.

Figure 5:
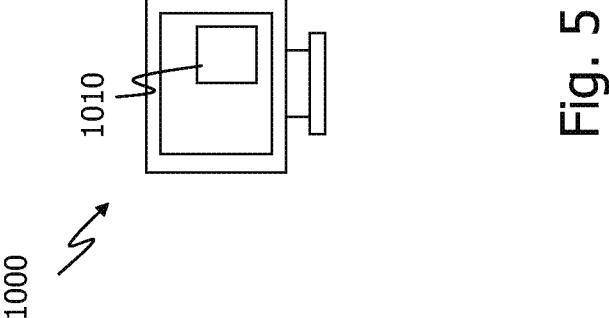
FIG. 5 illustrates a schematic representation of data processing system for detecting an unintended movement of a first tracker attached to a patient.

FIG. 5 illustrates a schematic representation of a data processing system 1000 for detecting an unintended movement of a tracker 100 attached to a patient anatomy 200. The data processing system 1000 comprises one or more processors 1010 configured to perform the steps of the flow diagrams 400, 700, 900 described herein. In some variants, the data processing system 1000 is built from cloud computing resources. In other variants, the data processing system 1000 is physically located in an operating room.

Figure 6:
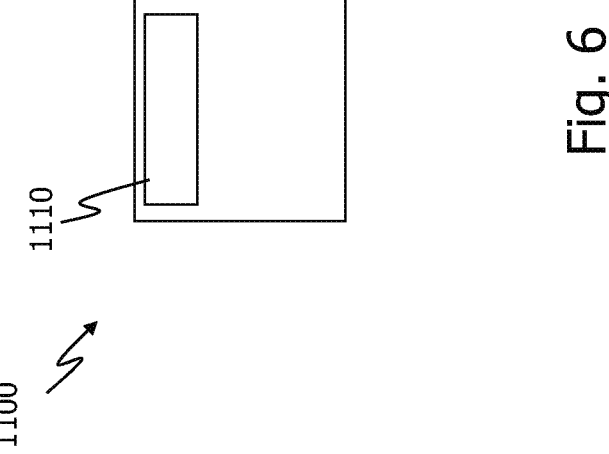
FIG. 6 illustrates a schematic representation of a computer program product configured to perform the steps of the method for detecting unintended movement of a patient tracker.

FIG. 6 illustrates a schematic representation of a computer program product 1100 comprising instructions 1110 configured to perform the steps of the methods of flow diagrams 400, 700, 900 when executed on one or more processors, e.g., on the one or more processors 1010 of the data processing system 1000 shown in FIG. 5.

Since the a detected tracker drift or impact can be indicative of a relative movement between a patient tracker 100 and a patient anatomy 200, the technique presented herein enables continuously maintaining a high registration quality. Any temporal interval a surgeon operates on the basis of an incorrect registration is minimized, since a possible time gap between an unintended tracker movement relative to the patient anatomy 200 and a re-registration for compensating the resulting inaccuracy can be minimized.

The invention claimed is:

1. A method for navigating a tracked surgical tool based on a re-registration of a first tracker coordinate system associated with a first tracker attached to a patient or image data thereof with a medical image coordinate system associated with medical image data of the patient, wherein the first tracker comprises a first acceleration sensor configured to generate inertial data indicative of an acceleration of the first tracker, a second tracker comprising a second acceleration sensor is attached to the patient, and a second tracker coordinate system associated with the second tracker or image data thereof has been registered with the medical image coordinate system, the method comprising the following steps performed by a processor:

receiving inertial data acquired by the first acceleration sensor of the first tracker;

analyzing the inertial data acquired by the first acceleration sensor, or data derived therefrom, to determine at least one first predetermined condition indicative of at least one of i) a drift of the first tracker; and ii) an impact on the first tracker;

receiving inertial data acquired by the second acceleration sensor of the second tracker;

analyzing the inertial data acquired by the second acceleration sensor, or data derived therefrom, to determine at least one second predetermined condition indicative of at least one of i) a drift of the second tracker; and ii) an impact on the second tracker;

re-registering the first tracker coordinate system with the medical image coordinate system based on the registration of the second tracker coordinate system with the medical image coordinate system, when the at least one first predetermined condition is fulfilled and the at least one second predetermined condition is not fulfilled; and navigating the tracked surgical tool based on the re-registration.

2. The method according to claim 1, wherein the at least one first predetermined condition comprises at least one threshold decision.

3. The method according to claim 2, wherein the at least one threshold decision is based on a first decision threshold of at least 5 m/s².

4. The method according to claim 3, wherein:

the inertial data received from the first acceleration sensor, or data derived therefrom, is indicative of an angular acceleration; and the at least one threshold decision is based on a second decision threshold based on the angular acceleration.

5. The method according to claim 2, wherein:

the inertial data received from the first acceleration sensor, or data derived therefrom, is indicative of an angular acceleration; and the at least one threshold decision is based on the angular acceleration.

6. The method according to claim 1, further comprising:

triggering a first re-registration notification when the at least one first predetermined condition is fulfilled and the at least one second predetermined condition is not fulfilled.

7. The method according to claim 6, wherein a notification device is configured to output the first re-registration notification.

8. The method according to claim 7, further comprising:

monitoring the notification device for the first re-registration notification; and generating at least one re-registration signal upon detecting the first re-registration notification.

9. The method according to claim 8, wherein the at least one re-registration signal triggers re-registering the first tracker coordinate system with the medical image coordinate system.

10. The method of claim 1, wherein the drift of the first tracker comprises at least one of a positional drift of the first tracker and an integration drift of the first acceleration sensor.

11. The method according to claim 1, wherein at least the first tracker is imaged in camera image data continuously taken by a camera system.

12. The method according to claim 11, the method comprising at least one of i) visualizing the camera image data at least for a point in time corresponding to a detected impact; and ii) analyzing the camera image data for a positional change of the first tracker, wherein the first tracker coordinate system is re-registered with the medical image coordinate system in case a positional change of the first tracker is identified based on the camera image data while the first predetermined condition is fulfilled.

13. The method according to claim 12, wherein the camera system comprises a third acceleration sensor configured to generate inertial data indicative of an acceleration of the camera system, wherein the method further comprises:

receiving, from the third acceleration sensor, inertial data; and analyzing the received inertial data, or data derived therefrom, to determine at least one third predetermined condition indicative of an impact on the camera system, wherein the first tracker coordinate system is re-registered with the medical image coordinate system in case the inertial data generated by the third acceleration sensor is not indicative of an impact on the camera system while the first predetermined condition is fulfilled, and a movement of the first tracker is identified based on the image data.

14. The method according to claim 11, wherein the camera system comprises a third acceleration sensor configured to generate inertial data indicative of an acceleration of the camera system, wherein the method further comprises:

receiving, from the third acceleration sensor, inertial data; and analyzing the received inertial data, or data derived therefrom, to determine at least one third predetermined condition indicative of an impact on the camera system, wherein the first tracker coordinate system is re-registered with the medical image coordinate system in case the inertial data generated by the third acceleration sensor is not indicative of an impact on the camera system while the first predetermined condition is fulfilled.

15. A computer program product comprising non-transitory computer readable medium including instructions configured to be executed on one or more processors to perform the steps of:

receiving inertial data acquired by a first acceleration sensor of a first tracker;

analyzing the inertial data acquired by the first acceleration sensor, or data derived therefrom, to determine at least one first predetermined condition indicative of at least one of i) a drift of the first tracker; and ii) an impact on the first tracker;

receiving inertial data acquired by a second acceleration sensor of a second tracker;

analyzing the inertial data acquired by the second acceleration sensor, or data derived therefrom, to determine at least one second predetermined condition indicative of at least one of i) a drift of the second tracker; and ii) an impact on the second tracker;

re-registering the first tracker coordinate system with the medical image coordinate system based on the registration of the second tracker coordinate system with the medical image coordinate system when the at least one first predetermined condition is fulfilled and the at least one second predetermined condition is not fulfilled; and navigating the tracked surgical tool based on the re-registration.

16. A surgical system for navigating a tracked surgical tool based on a re-registration of a first tracker coordinate system associated with a first tracker attached to a patient or image data thereof with a medical image coordinate system associate with medical image data of the patient, wherein the first tracker comprises a first acceleration sensor configured to generate inertial data indicative of an acceleration of the first tracker, a second tracker comprising a second acceleration sensor is attached to the patient, and a second tracker coordinate system associated with the second tracker or image data thereof has been registered with the medical image coordinate system, the system comprising a processor configured for:

receiving inertial data acquired by the first acceleration sensor of the first tracker;

analyzing the inertial data acquired by the first acceleration sensor, or data derived therefrom, to determine at least one first predetermined condition indicative of at least one of i) a drift of the first tracker; and ii) an impact on the first tracker;

receiving inertial data acquired by the second acceleration sensor of the second tracker;

analyzing the inertial data acquired by the second acceleration sensor, or data derived therefrom, to determine at least one second predetermined condition indicative of at least one of i) a drift of the second tracker; and ii) an impact on the second tracker;

re-registering the first tracker coordinate system with the medical image coordinate system based on the registration of the second tracker coordinate system with the medical image coordinate system when the at least one first predetermined condition is fulfilled and the at least one second predetermined condition is not fulfilled; and navigating the tracked surgical tool based on the re-registration.

17. The surgical system of claim 16, further comprising a camera system configured to image at least the first tracker that is imaged in camera image data continuously taken by the camera system.

\* \* \* \* \*